(12) United States Patent
Catinat et al.

(10) Patent No.: US 6,603,027 B1
(45) Date of Patent: Aug. 5, 2003

(54) CATALYST BASED ON ZELOLITE, USE AND EPOXIDATION METHOD IN THE PRESENCE OF THIS CATALYST

(75) Inventors: Jean-Pierre Catinat, Waudrez (BE); Michel Strebelle, Brussels (BE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 09/555,454

(22) PCT Filed: Nov. 23, 1998

(86) PCT No.: PCT/EP98/07530

§ 371 (c)(1),
(2), (4) Date: May 31, 2000

(87) PCT Pub. No.: WO99/28035

PCT Pub. Date: Jun. 10, 1999

(30) Foreign Application Priority Data

Dec. 1, 1997 (BE) ............................................. 9700973

(51) Int. Cl.$^7$ .......................... B01J 29/89; C07D 301/06
(52) U.S. Cl. ...................... 549/533; 549/531; 549/523; 502/64; 502/71; 502/72
(58) Field of Search .............................. 502/64, 71, 77, 502/242; 549/533, 531, 55, 523

(56) References Cited

U.S. PATENT DOCUMENTS

| 4,952,545 | A | * | 8/1990 | Imanari et al. ................ 502/73 |
| 5,932,750 | A | * | 8/1999 | Hayashi et al. ............. 549/523 |
| 6,054,112 | A | * | 4/2000 | Hasenzahl et al. .......... 423/705 |
| 6,380,407 | B1 | * | 4/2002 | Catinat et al. .............. 549/531 |

FOREIGN PATENT DOCUMENTS

EP   0 100 119   2/1984

OTHER PUBLICATIONS

B. Notari, "Titantium Silicalite: A New selective oxidation catalyst", R.K. Grasselli & A. W. Sleight Editors, Elsevier, 1991, pp. 243–256.

A. Van der Pol & J. Van Hooff, Applied Catalysis A, 1992, vol. 92, pp. 93–111.

* cited by examiner

*Primary Examiner*—Tom Dunn
*Assistant Examiner*—Christina Ildebrando
(74) *Attorney, Agent, or Firm*—Larson & Taylor PLC

(57) ABSTRACT

The invention relates to a catalyst obtained by deposition of a zeolite of TS-1 type on an inert honeycomb-shaped support which can be used in liquid-phase reactions for the epoxidation of olefins under the action of hydrogen peroxide.

9 Claims, No Drawings

CATALYST BASED ON ZELOLITE, USE AND EPOXIDATION METHOD IN THE PRESENCE OF THIS CATALYST

The invention relates to a novel zeolite-based supported catalyst. It also relates to a process for the manufacture of such a catalyst and to its use in liquid-phase chemical reactions, such as the epoxidation reaction of olefins under the action of hydrogen peroxide.

It is known to use a zeolite as catalyst in olefin epoxidation reactions. Thus, Patent Application EP 100,119 discloses a process for the epoxidation of olefins by means of hydrogen peroxide in the presence of a synthetic zeolite comprising titanium atoms. This synthetic zeolite comprising titanium atoms is known under the name of titanium silicalite and is abbreviated to TS-1.

It is also known that zeolites become deactivated with use and that, consequently, it is necessary regularly to carry out regeneration treatments, generally by washing with solvents or by heating, in order to restore the activity thereof. It is important for the zeolite not to degrade under the regeneration conditions.

It is also known that zeolites, in particular TS-1 obtained according to the process disclosed in the abovementioned patent application, can be composed of very fine particles which it is difficult to separate from the reaction mixture in order to carry out the regeneration thereof. Furthermore, when zeolites, in particular TS-1, are composed of coarse grains, a significant decrease in the catalytic activity of this catalyst, on the one hand, and a poor resistance to attrition of the particles, on the other hand, are observed.

The aim of the invention is to overcome these disadvantages by providing a novel catalyst which has a shape such that it is easy to separate from the reaction mixture, in order to carry out the regeneration thereof, and which exhibits good mechanical properties and a high activity.

The subject-matter of the invention is a catalyst comprising a zeolite deposited on a honeycomb-shaped support. "Honeycomb-shaped" is understood to denote a shape composed of components with a cellular structure, whatever the shape of the cells. The catalyst according to the invention has a level of catalytic activity similar to that of a fine powder and can be regenerated without significant loss of zeolite or of the catalytic activity. More particularly, it has been found that the deposition of a zeolite on a honeycomb-shaped support makes it possible to achieve a very high level of activity, comparable with the level of activity of the fine powder, without, however, having the disadvantages thereof.

The honeycomb-shaped support is advantageously composed of an inert material which withstands the regeneration conditions and on which it is possible to make the zeolite adhere by means of a binder. Silicas are highly suitable as support. It can relate, for example, to silicas combined with other magnesium or aluminium oxides and their mixtures. The support is preferably cordierite or mullite. A particular preference is shown for cordierite because it results in better adhesion of the zeolite to the support. When the catalyst is subsequently regenerated in the presence of an oxidizing agent, such as hydrogen peroxide, a preference is shown for mullite because it exhibits better resistance to such regeneration conditions, which result in acidification of the medium. However, cordierite can also be regenerated in the presence of an oxidizing agent, provided that the pH is maintained during the regeneration at a value of 3 to 4 approximately.

The honeycomb-shaped support is generally provided in the form of a cartridge comprising from 10 to 1200 cells per $inch^2$ ($cpi^2$). The number of cells is preferably from 50 to 450 $cpi^2$, for example from 70 to 400 $cpi^2$.

Zeolite is understood to denote a solid comprising silica which exhibits a microporous crystalline structure. The zeolite is advantageously devoid of aluminium. The zeolite can comprise titanium. The zeolite according to the invention is preferably a zeolite in which several silicon atoms have been replaced by titanium atoms.

Good results have been obtained with zeolites of titanium silicalite type. The latter advantageously exhibit a crystalline structure of ZSM-5, ZSM-11 or MCM-41 type or of beta type. They preferably exhibit an infrared absorption band at approximately 950–960 $cm^{-1}$.

Those corresponding to the formula $xTiO_2(1-x)SiO_2$ in which x is from 0.0001 to 0.5, preferably from 0.001 to 0.05, are highly effective. Materials of this type, known under the name of TS-1, exhibit a microporous crystalline zeolite structure analogous to that of the zeolite ZSM-5. The properties and the main applications of these compounds are known (B. Notari, Structure-Activity and Selectivity Relationship in Heterogeneous Catalysis, R. K. Grasselli and A. W. Sleight Editors, Elsevier, 1991, p. 243–256). Their synthesis has been studied in particular by A. Van der Poel and J. Van Hooff (Applied Catalysis A, 1992, Volume 92, pages 93–111) and by Thangaraj et al. (Zeolites, 12 (1992), 943–950).

The zeolite content in the catalyst according to the invention, expressed as percentage by weight of zeolite in the catalyst, is generally greater than or equal to 1% and less than or equal to 60%. The zeolite content is preferably greater than or equal to 5% and less than or equal to 40%.

The catalyst according to the invention withstands, during phases of conditioning the catalyst or of regeneration, dry heating operations (at 500° C., for example) or heating operations in the presence of solvent, without significant loss of active elements. In addition, hydrogen peroxide, used as oxidizing reactant during the synthesis or as regeneration agent, does not cause significant damage to the catalyst either.

The invention also relates to a process for the manufacture of the above-described catalyst. According to this process, the zeolite is, in a first stage, dispersed in a binder and, in a second stage, the dispersion thus obtained is deposited by impregnation on a honeycomb-shaped support.

The binder employed is generally a silicon-based compound. Mention may be made, by way of examples, of colloidal silicas, silica sols, silicates (for example, tetraalkyl silicates) and silicone resins. Colloidal silicas are preferred. Several grades of colloidal silica may be suitable. They are characterized in particular by the size of the particles, by their specific surface, by their pH and by the nature of the counterion.

The size of the colloidal silica particles is generally between 1 and 30 $\mu$m. The size of the particles is preferably between 5 and 25 $\mu$m. There is a marked preference for particles with a size of between 7 and 20 $\mu$m.

Excessively fine zeolite particles result in a troublesome thixotropy. Excessively coarse particles result in a sedimentation which is too fast for efficient use. The size of the particles is generally greater than or equal to 0.1 μm and less than or equal to 10 μm. The size of the particles is advantageously greater than or equal to 1 μm and less than or equal to 5 μm.

The colloidal silicas can exhibit an acidic or basic pH. When the pH is acidic, the counterion is advantageously a chloride anion and/or the silica particles can be covered at the surface with a layer of alumina. When the pH is alkaline, the counterion is advantageously a sodium cation or an ammonium cation and/or surface silicon atoms can be replaced by aluminium atoms.

In the first stage of the process according to the invention, a dispersion of the zeolite in a binder is prepared, optionally with stirring. The ratio by weight of the amount of zeolite charged to the amount of binder can vary within a very wide proportion. This ratio is generally less than or equal to 20 and greater than or equal to 0.1. This ratio is preferably less than or equal to 15 and greater than or equal to 0.5. A ratio in the region of 10 makes it possible to limit the amount of material to be deposited on the honeycomb-shaped support while fixing the desired amount of zeolite, without, however, blocking the channels of the support.

It can be advantageous to add water thereto. The amount of water in the dispersion is generally such that the dispersion comprises at least 10 g of zeolite per 100 g of water. The amount of water is advantageously such that the dispersion comprises at least 20 g of zeolite per 100 g of water. This concentration is generally less than or equal to 175 g of zeolite per 100 g of water. This concentration is advantageously less than 150 g of zeolite per 100 g of water. A particular preference is shown for a range of concentrations from 50 to 90 g of zeolite per 100 g of water.

The honeycomb-shaped support is generally impregnanted either by pouring the dispersion onto the honeycomb-shaped support or by immersing the support in the dispersion. The impregnation stage generally takes place at room temperature. After the impregnation stage, the liquid adhering to the walls of the honeycombs can be driven off with a jet of compressed air, in order to prevent the channels in the honeycombs from blocking. The operation can optionally be repeated. The honeycomb-shaped support can subsequently be dried (for example, exposed to the surrounding air) for a period of time generally varying from a few minutes to a few hours, preferably for a period of between 30 minutes and 180 minutes. The impregnated support can subsequently be dried (for example, in a ventilated oven) at a temperature greater than or equal to 105° C. and less than or equal to 300° C., preferably greater than or equal to 180° C. and less than or equal to 2500° C. The duration of the drying of the impregnated support is generally greater than or equal to 2 hours and less than or equal to 3 days. This duration is preferably greater than or equal to 12 hours and less than or equal to 2 days.

The impregnation operation can be repeated several times, optionally with intermediate drying. The successive impregnations can be carried out under the same conditions as described above, in order to deposit several layers of zeolite on the support. It is preferable to operate with concentrated solutions of TS-1, in order to limit the number of impregnation stages in order to reach a given amount of deposited TS-1. However, while it is generally advantageous to use a concentrated solution for the deposition of the first impregnation layer, it has been found that it may be preferable to use more dilute solutions for the impregnation layers deposited subsequently. On completion of the final impregnation, the catalyst can be calcined (for example, in a static furnace) at a temperature greater than or equal to 200° C. and less than or equal to 800° C. This temperature is preferably greater than or equal to 300° C. and less than or equal to 600° C. This temperature is advantageously greater than or equal to 400° C. and less than or equal to 550° C. The calcination time is generally between a few hours and several days. This drying time is preferably greater than or equal to 6 hours and less than or equal to 12 hours.

The amount of material deposited on the honeycomb-shaped support comprises the amount of zeolite deposited as well as the amount of binder used. The amount of material deposited on the honeycomb-shaped support depends mainly on the size of the support. For example, for honeycombs comprising 400 cells per inch$^2$, the increase in weight is generally greater than or equal to 10% and less than or equal to 80%. The increase in weight is preferably greater than 20% and less than or equal to 70%. The increase in weight is advantageously greater than or equal to 30% and less than or equal to 55%.

The desired amount of catalyst is generally achieved by the deposition of 3 to 5 layers of dispersion on the honeycomb-shaped support. For the same amount of material deposited, the increase in the number of layers results in better adhesion of the deposit to the support.

Adhesion of the zeolite layer to the honeycomb-shaped support can be promoted by preimpregnation of the said support with the pure binder. Likewise, the support can be pretreated in acidic or basic medium, according to the nature of the support, in order to obtain greater deposition during the first impregnation stage. A surface-active agent can also be added to the dispersion in order to increase the amount of material deposited during the first impregnation.

The catalyst according to the invention can be regenerated after several reaction cycles, generally by heat treatment, by washing or by treatment by means of an oxidixing agent, such as hydrogen peroxide, and thus regain a level of activity and a selectivity which are similar to those of the fresh catalyst.

The catalyst according to the invention can generally be used in liquid-phase chemical reactions, such as, for example, oxidation or epoxidation reactions. The invention consequently also relates to the use of a catalyst comprising a zeolite deposited on a honeycomb-shaped support in liquid-phase chemical reactions.

The catalyst according to the invention is particularly well suited to liquid-phase reactions for the epoxidation of olefins by a peroxide compound. The products obtained are the corresponding epoxides (or oxiranes). The process of the present invention applies to all aliphatic or alicyclic olefins, whatever the number of carbon atoms in the carbon-comprising chain, the position of the unsaturation and the presence of a functional chemical group in the chain. Mention may be made, as non-limiting example of olefin which can be used in the process according to the present invention, of ethylene, propylene, allyl chloride, 1-butene, 2-butene, 1-octene, cyclohexene, cyclooctene and mesityl oxide. Allyl chloride and propylene are particularly well suited to the synthesis of epichlorohydrin or propylene oxide. The peroxide compound is preferably hydrogen peroxide.

A reaction solvent is usually added in order to allow the olefin and hydrogen peroxide to be brought into contact. Methanol is preferred among the possible solvents.

The catalyst according to the present invention is generally used in a continuous or batchwise process. A continuous process is preferred.

The reaction temperature is generally greater than or equal to 0° C. and less than or equal to 100° C. This temperature is preferably greater than or equal to 5° C. and less than or equal to 50° C. This temperature is advantageously greater than or equal to 10° C. and less than or equal to 40° C.

The residence time is the ratio of the empty reactor volume to the feed flow rate. The residence time per reactor is generally greater than or equal to 1 minute and less than or equal to 100 minutes. The residence time is preferably greater than or equal to 5 minutes and less than or equal to 80 minutes. The residence time is advantageously greater than or equal to 10 minutes and less than or equal to 50 minutes.

The molar ratio of the amount of olefin charged to the amount of hydrogen peroxide is generally greater than or equal to 1 and less than or equal to 20. This ratio is preferably greater than or equal to 1.5 and less than or equal to 10.

The molar ratio of the amount of olefin charged to the amount of solvent is generally greater than or equal to 2 and less than or equal to 50. This ratio is preferably greater than or equal to 5 and less than or equal to 10.

In the examples which follow, the degree of conversion of the hydrogen peroxide is given by the equation:

DC=1−(the number of moles of hydrogen peroxide recovered divided by the number of moles of hydrogen peroxide employed); it is expressed as a percentage, the selectivity is given by the ratio of the amount of epoxide obtained to the sum of all the products formed, the amount of epoxide formed is the amount formed after the time necessary for the degree of conversion of the hydrogen peroxide, after the reaction has been running for one hour, to have fallen to 75% of this value.

The invention is more fully illustrated in the following non-limiting examples.

EXAMPLE 1

In this example, a catalyst was prepared comprising TS-1 deposited on a honeycomb-shaped support.

The details of the preparation of the catalyst are combined in Table I below.

TABLE I

| | |
|---|---|
| Diameter of the TS-1 particles | 2.1 μm |
| Nature of the binder | Silica sol |
| Material of the support | Cordierite |
| Honeycomb employed | 2 cartridges |
| | h = 10 cm, ø = 2.6 cm |
| Number of cells/inch$^2$ | 400 |
| Starting weight of the support (g) | 46.5 |
| Concentration of TS-1 in the dispersion (g/100 g H$_2$O) | 90 (1st layer) |
| | 50 (2nd layer) |
| Increase in weight at the 1st impregnation (g) | 7.9 |
| Increase in weight at the 2nd impregnation (g) | 6.3 |
| Intermediate drying | 18 h at 180° C. |
| Calcination | 6 h at 500° C. |
| Total increment in weight of the support (g) | 14.2 |
| TS-1/binder ratio (g) | 51.5/48.5 |

EXAMPLES 2 to 4

The catalyst obtained in Example 1 was used in epoxidation reactions.

The plant comprises two thermostatically-controlled, vertical, tubular reactors arranged in a cascade. Two catalyst cartridges are placed in each reactor. Each reactor is equipped with a loop and a pump which allows the liquid to be recirculated over the catalyst. Control of the temperature is provided by a coil in each reactor, through which coil runs an oil which is regulated in temperature.

7.3 grams of TS-1, deposited on the two cartridges, were placed in each 125 ml reactor equipped with a recirculation loop (total volume=300 ml). The first reactor is fed continuously at a given flow rate with a solution of allyl chloride and of hydrogen peroxide in methanol (allyl chloride/H$_2$O$_2$=2 mol/mol; H$_2$O$_2$ concentration of 1.33 mol/kg) at a temperature of T° C. The mixture of reactants (olefin, hydrogen peroxide and methanol) is prepared immediately before it is introduced at a constant flow rate at the top of the first reactor.

The linear rate of passage of the solution recirculating in the reactor was adjusted to 0.94 m/min and the recirculation flow rate is of the order of 30 litres/hour.

The duration of the tests was set on the basis of a decrease of 25% in the initial activity of the catalyst in the first reactor after the reaction has been running for one hour.

Under these conditions, at a given temperature and for a defined residence time, the allyl chloride is converted into epichlorohydrin.

The conditions and the results of the tests carried out are taken up in Table II.

TABLE II

| | Conditions | | | Results Outlet of the 2nd reactor | | Amount of epichloro- hydrin formed (g) |
|---|---|---|---|---|---|---|
| Ex. | Tempera- ture T (° C.) | Residence time reactor (min) | Feed flow rate (ml/h) | DC ($H_2O_2$) (%) | Epichloro- hydrin selectivity | |
| 2 | 40 | 40 | 187 | 99.4 | 89.7 | 238 |
| 3 | 10 | 20 | 375 | 77.0 | 99.1 | 150 |
| 4 | 25 | 50 | 150 | 98.4 | 95.1 | 218 |

Propylene, which is then introduced in the gas form into the reactor, is analogously converted into propylene oxide.

What is claimed is:

1. An epoxidation catalyst comprising a zeolite containing titanium in the framework deposited on a honeycomb-shaped support by impregnation with the aid of a binder.

2. The catalyst according to claim 1, in which the titanium containing zeolite is titanium silicalite.

3. The catalyst according to claim 2, in which the titanium containing zeolite is TS-1.

4. A process for the manufacture of an epoxidation catalyst comprising a zeolite containing titanium in the framework deposited on a honeycomb-shaped support by impregnation with the aid of a binder, according to which, in a first stage, the titanium containing zeolite is dispersed in the binder and, in a second stage, the dispersion thus obtained is deposited on a honeycomb-shaped support.

5. The process according to claim 4, in which the binder is a colloidal silica.

6. The process according to claim 4, in which the ratio by weight of the amount of titanium containing zeolite employed to the amount of binder employed is less than or equal to 20 and greater than or equal to 0.1.

7. The process according to claim 4, in which the impregnation of the support is carried out in several stages, optionally with intermediate drying.

8. The process according to claim 4, in which the support is treated with the binder before the impregnation stage.

9. Process for the manufacture of epoxides, preferably epichlorohydrin or propylene oxide, by reaction between an olefin, preferably allyl chloride or propylene, and a peroxide compound, preferably hydrogen peroxide, in the presence of a catalyst comprising a zeolite containing titanium in the framework deposited on a honeycomb-shaped support by impregnation with the aid of a binder.

* * * * *

UNITED STATES PATENT AND TRADEMARK OFFICE
CERTIFICATE OF CORRECTION

PATENT NO.    : 6,603,027 B1
DATED         : August 5, 2003
INVENTOR(S)   : Catinat et al.

It is certified that error appears in the above-identified patent and that said Letters Patent is hereby corrected as shown below:

<u>Title page, Item [54] and Column 1, lines 1-3,</u>
Should read:
-- CATALYST BASED ON ZEOLITE, USE AND EPOXIDATION METHOD IN THE PRESENCE OF THIS CATALYST --

Signed and Sealed this

Eleventh Day of November, 2003

JAMES E. ROGAN
*Director of the United States Patent and Trademark Office*